United States Patent [19]
Gaster et al.

[11] Patent Number: 5,919,932
[45] Date of Patent: Jul. 6, 1999

[54] BIPHENYLAMIDE DERIVATIVES AS $5HT_{1D}$ ANTAGONISTS

[75] Inventors: Laramie Mary Gaster, Bishop's Stortford; Keith Raymond Mulholland, Harlow, both of United Kingdom

[73] Assignee: SmithKline Beecham p.l.c., Brentford, United Kingdom

[21] Appl. No.: 08/930,848

[22] PCT Filed: Apr. 2, 1996

[86] PCT No.: PCT/EP96/01465

§ 371 Date: Oct. 7, 1997

§ 102(e) Date: Oct. 7, 1997

[87] PCT Pub. No.: WO96/31508

PCT Pub. Date: Oct. 10, 1996

[30] Foreign Application Priority Data

Apr. 7, 1995 [GB] United Kingdom .................. 9507203

[51] Int. Cl.⁶ .......................... A61K 31/46; A61K 31/47; C07D 451/06; C07D 451/04
[52] U.S. Cl. .......................... 546/112; 514/299; 514/304; 514/361; 546/121; 546/126; 548/131
[58] Field of Search ............................. 548/131; 546/121, 546/112, 126; 514/299, 304, 361

[56] References Cited

U.S. PATENT DOCUMENTS

| | | | |
|---|---|---|---|
| 5,124,460 | 6/1992 | Humphrey | 548/131 |
| 5,132,316 | 7/1992 | Hadley et al. | 514/361 |
| 5,138,064 | 8/1992 | Murata et al. | 548/127 |
| 5,326,776 | 7/1994 | Winn et al. | 514/382 |

FOREIGN PATENT DOCUMENTS

| | | | |
|---|---|---|---|
| 0239309 | 9/1987 | European Pat. Off. | 548/131 |
| 0307140 | 3/1989 | European Pat. Off. | 548/131 |
| 0375450 | 6/1990 | European Pat. Off. | 548/131 |
| 0398629 | 11/1990 | European Pat. Off. | 548/131 |
| 0497121 | 8/1992 | European Pat. Off. | 548/131 |
| 0 533 266 A1 | 9/1992 | European Pat. Off. . | |
| 0 533 267 A1 | 9/1992 | European Pat. Off. . | |
| 0 533 268 A1 | 9/1992 | European Pat. Off. . | |
| 2229182 | 9/1990 | United Kingdom | 548/131 |
| 2 276 160 | 3/1993 | United Kingdom . | |
| 2 276 162 | 3/1993 | United Kingdom . | |
| 2 273 930 | 12/1993 | United Kingdom . | |
| WO 94/15920 | 7/1994 | WIPO . | |
| WO 95/04729 | 2/1995 | WIPO . | |
| WO 95/06044 | 3/1995 | WIPO . | |
| WO 95/06637 | 3/1995 | WIPO . | |
| WO 95/06644 | 3/1995 | WIPO . | |
| WO 95/26328 | 10/1995 | WIPO . | |
| WO 96/06079 | 2/1996 | WIPO . | |

OTHER PUBLICATIONS

J. Med. Chem., Clitherow, et al., vol. 37, No. 15, 1994, pp. 2253–2257.
P. Saxena, Pharmoc. Ther; 1995, vol. 66, pp. 339–368.

*Primary Examiner*—Floyd D. Higel
*Attorney, Agent, or Firm*—Wayne J. Dustman; William T. King; Charles M. Kinzig

[57] ABSTRACT

Biphenyl amide derivatives as $5HT_{1D}$ antagonists, processes for their preparation, pharmaceutical compositions containing them and their use for the treatment of CNS disorders.

13 Claims, No Drawings

BIPHENYLAMIDE DERIVATIVES AS 5HT$_{1D}$ ANTAGONISTS

This application is a 371 of PCT/EP96/01465 filed Apr. 2, 1996.

The present invention relates to novel amide derivatives, processes for their preparation, and pharmaceutical compositions containing them.

J. Med. Chem., vol 37, 1984, 2253–57, EPA 0 533 266/7/8, WO94/15920, WO95/04729, WO95/06637, WO95/06644, WO95/06044, WO95/26328, WO95/06079, GBA-2 276 160, GBA-2 276 162, GBA-2 276 164 and GBA-2 273 930 all disclose a series of benzanilide derivatives which are said to possess 5HT$_{1D}$ receptor antagonist activity. These compounds are said to be of use in the treatment of various CNS disorders.

A structurally distinct class of compounds have now been discovered and have been found to exhibit 5HT$_{1D}$ receptor antagonist activity. In a first aspect, the present invention therefore provides a compound of formula (I) or a salt or N-oxide thereof:

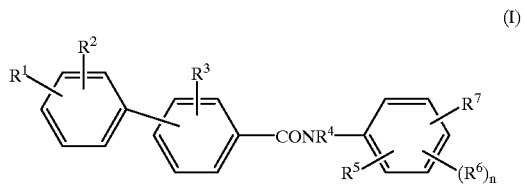

(I)

in which
R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, CONHNR$^{10}$R$^{11}$, NR$^{10}$R$^{11}$, NR$^{10}$CO$_2$R$^{11}$, NR$^{10}$CO(CH$_2$)$_a$NR$^{10}$R$^{11}$, NR$^{10}$CONR$^{10}$R$^{11}$, CR$^{10}$=NOR$^{11}$, CNR$^{10}$=NOR$^{11}$, where R$^9$, R$^{10}$ and R$^{11}$ are independently hydrogen or C$_{1-6}$alkyl and a is 1 to 4 or R$^1$ is an optionally substituted 5 to 7-membered heterocyclic ring containing 1 to 3 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl;

R$^4$ is hydrogen or C$_{1-6}$alkyl and R$^5$ is hydrogen, halogen, hydroxy, C$_{1-6}$alkyl or C$_{1-6}$alkoxy or R$^4$ and R$^5$ together form a group —A— where A is (CR$^{12}$R$^{13}$)$_q$ where q is 2, 3 or 4 and R$^{12}$ and R$^{13}$ are independently hydrogen or C$_{1-6}$alkyl or A is (CR$^{12}$R$^{13}$)$_r$—D where r is 0, 1, 2 or 3 and D is oxygen, sulphur or CR$^{12}$=CR$^{13}$;

R$^6$ is hydrogen, halogen, hydroxy, C$_{1-6}$alkyl or C$_{1-6}$alkoxy;

n is 1 or 2; and

R$^7$ is an optionally substituted 6,6 or 6,5 bicyclic ring containing a nitrogen atom and optionally a further heteroatom selected from from oxygen, nitrogen or sulphur.

C$_{1-6}$alkyl groups, whether alone or as part of another group, may be straight chain or branched.

Suitably R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, CONHNR$^{10}$R$^{11}$, NR$^{10}$R$^{11}$, NR$^{10}$CO$_2$R$^{11}$, NR$^{10}$CO(CH$_2$)$_a$NR$^{10}$R$^{11}$, NR$^{10}$CONR$^{10}$R$^{11}$, CR$^{10}$=NOR$^{11}$, CNR$^{10}$=NOR$^{11}$, where R$^9$, R$^{10}$ and R$^{11}$ are independently hydrogen or C$_{1-6}$alkyl and a is 1 to 4.

When R$^1$ is an optionally substituted 5 to 7-membered heterocyclic ring containing 1 to 3 heteroatoms selected from oxygen, nitrogen or sulphur, suitable heterocyclic rings include thienyl, furyl, pyrrolyl, triazolyl, diazolyl, imidazolyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Preferably R$^1$ is oxadiazolyl, most preferably a 5-methyl-1,2,4-oxadiazol-3-yl group.

Suitably R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are hydrogen or C$_{1-6}$alkyl. Preferably R$^2$ is C$_{1-6}$alkyl, in particular methyl. Preferably R$^3$ is hydrogen.

Suitably R$^4$ is hydrogen or C$_{1-6}$alkyl and R$^5$ is hydrogen, halogen, hydroxy, C$_{1-6}$alkyl or C$_{1-6}$alkoxy or R$^4$ and R$^5$ together form a group —A— where A is (CR$^{12}$R$^{13}$)$_q$ where q is 2, 3 or 4 and R$^{12}$ and R$^{13}$ are independently hydrogen or C$_{1-6}$alkyl or A is (CR$^{12}$R$^{13}$)$_r$—D where r is 0, 1, 2 or 3 and D is oxygen, sulphur or CR$^{12}$=CR$^{13}$. Preferably R$^4$ and R$^5$ are both hydrogen or R$^4$ and R$^5$ are linked to form a group A. Preferably A is (CR$^{12}$R$^{13}$)$_q$ where R$^{12}$ and R$^{13}$ are both hydrogen and q is 2 or 3 such that A forms an ethyl or propyl linkage.

Suitably R$^6$ is hydrogen, halogen, hydroxy, C$_{1-6}$alkyl or C$_{1-6}$alkoxy. Preferably R$^6$ is C$_{1-6}$alkoxy, in particular methoxy. Suitably n is 1 or 2, preferably n is 1.

Suitably R$^7$ is a 6,6 or 6,5 bicyclic ring containing a nitrogen atom and optionally a further heteroatom selected from from oxygen, nitrogen or sulphur. Examples of such groups include tropane, isoquinuclidine and granatane rings. Optional substituents for such ring systems include C$_{1-6}$alkyl, such as methyl. For example, R$^7$ groups containing a nitrogen atom can be substituted on the nitrogen atom by a methyl group.

The groups R$^1$, R$^2$ and R$^3$ can be attached to their respective rings at any suitable position.

Particularly preferred compounds of the invention include:

N-[3-(8-Azabicyclo[3.2.1]octan-3-yl)-4-methoxyphenyl]-2'-methyl-4'-(5-methyl-1,2,4-oxadiazol-3-yl)biphenyl-4-carboxamide, N-[4-Methoxy-3-(8-methyl-8-azabicyclo[3.2.1]octan-3-yl)phenyl]-2'-methyl-4'-(5-methyl-1,2,4-oxadiazol-3-yl)biphenyl-4-carboxamide,

[3,4-Dihydro-6-methoxy-7-(8-methyl-8-azabicyclo[3.2.1]octan-3-yl)-2H-quinolin-1-yl]-[2'-methyl-4'-(5-methyl-1,2,4-oxadiazol-3-yl)biphenyl-4-yl]methanone,

[7-(8-Azabicyclo[3.2.1]octan-3-yl)-3,4-dihydro-6-methoxy-2H-quinolin-1-yl]-[2'-methyl-4'-(5-methyl-1,2,4-oxadiazol-3-yl)biphenyl-4-yl]methanone, N-[3-(8-Methyl-8-azabicyclo[3.2.1]octan-3-yl)phenyl]-2'-methyl-4'-(5-methyl-1,2,4-oxadiazol-3-yl)biphenyl-4-carboxamide, and pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers of compounds of formula (I) and mixtures thereof also form an aspect of the invention.

In a further aspect the present invention provides a process for the preparation of a compound of formula (I) which comprises:

(a) for compounds where $R^4$ is hydrogen or $C_{1-6}$alkyl and $R^5$ is hydrogen, halogen, hydroxy, $C_{1-6}$alkyl or $C_{1-6}$alkoxy, reaction of a compound of formula (II):

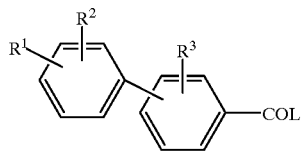

(II)

in which $R^1$, $R^2$ and $R^3$ are as defined in formula (I) and L is a leaving group, with a compound of formula (III):

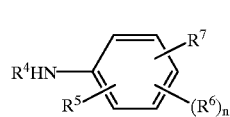

(III)

in which $R^4$ and $R^5$ are as defined above and $R^6$, $R^7$ and n are as defined in formula (1); or (b) where $R^4$ together with $R^5$ forms a group A, reaction of a compound of formula (II) as defined above with a compound of formula (IV):

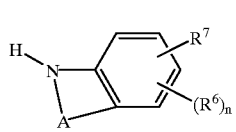

(IV)

in which A is as defined above and $R^6$, $R^7$ and n are as defined in formula (I); and optionally after (a) or (b) and in any order:
   converting a compound of formula (I) into another compound of formula (I)
   forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazide. Preferably the group L is halo, particularly chloro.

Alternatively L is an ester forming group such that the resulting esters of formula (II) can be reacted with compounds of formula (III) in the presence of an organoaluminium reagent such as trimethylaluminium. Such a reaction is typically carried out in the presence of an inert solvent such as toluene.

A compound of formula (II) is typically reacted with a compound of formula (III) or (IV) in an inert organic solvent such as DMF, THF or dichloromethane at ambient or elevated temperature in the presence of a base such as triethylamine or pyridine. Compounds of formula (II) can be prepared from a compound of formula (V):

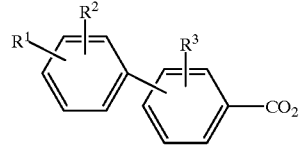

(V)

in which $R^1$, $R^2$ and $R^3$ are as defined in formula (I) using standard procedures. For example acid chlorides can be prepared by reaction with phosphorous pentachloride, oxalyl chloride or thionyl chloride. Acid anhydrides can be prepared by reaction with a suitable acid anhydride, for example trifluoroacetic anhydride.

Intermediate compounds of formula (V) are commercially available or can be prepared using standard procedures such as those outlined in EPA 533266/7/8 and GB A 2 276 160. Intermediate compounds of formulae (III) and (IV) can be prepared using standard procedures known in the art. Certain intermediate compounds of formulae (III) and (IV) are novel and form a further aspect of the invention.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

Certain compounds of formula (I) can be converted into further compounds of formula (I) using standard procedures.

$5HT_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder, memory disorders, including dementia, amnestic disorders and age-associated memory impairment; and disorders of eating behaviors, including anorexia nervosa and bulimia nervosa. Other CNS disorders include motor disorders such as Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavorings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following example illustrate the invention.

DESCRIPTION 1

3-Hydroxy-3-(2-methoxyphenyl)-8-methyl-8-azabicyclo[3.2.1]octane

A stirred solution of 2-bromoanisole (9.25 ml, 0.074 mol) in dry diethyl ether (110 ml) under argon was cooled to 0° C. and was treated with n-butyllithium (1.6M) (45.6 ml, 0.073 mol) slowly. The reaction mixture was then allowed to warm to room temp. After 0.5 h, a solution of tropinone (10.14 g, 0.073 mol) in dry diethyl ether (60 ml) was added causing the reaction mixture to reflux. Reflux was maintained for a further 0.5 h, before the reaction mixture was allowed to cool. Water (40 ml) was then added and the reaction mixture was stirred for 0.25 h. The organic layer was then separated, dried ($Na_2SO_4$) and evaporated under reduced pressure to give a pale yellow oily solid, which was triturated with petroleum ether (60–80). The resultant suspension was then filtered to give the title compound as a white solid, which was dried in vacuo (9.04 g, 50%).

$^1$H NMR (250 MHz, $CDCl_3$) δ (ppm): 7.32 (dd, 1H), 7.20 (m, 1H), 6.90 (m, 2H), 4.01 (s, 1H), 3.89 (s, 3H), 3.22 (m, 2H), 2.41 (m, 1H), 2.35 (s, 3H), 2.30 (m, 3H), 2.02 (m, 4H)

DESCRIPTION 2

3-(2-Methoxyphenyl)-8-methyl-8-azabicyclo[3.2.1]octane

The product from Description 1 (8.00 g, 0.032 mol) was added slowly to trifluoroacetic acid (80 ml) with stirring and heated to reflux. After 11 h, the reaction mixture was evaporated under reduced pressure and partitioned between 10% NaOH and $CH_2Cl_2$. The aqueous layer was then extracted with $CH_2Cl_2$ (2×) and the combined organic layers were dried ($Na_2SO_4$) and evaporated under reduced pressure to give a yellow oil which was dried in vacuo. The oil was redissolved in ethanol (100 ml) and was hydrogenated at atmospheric pressure in the presence of 10% PdC (1 g) at 40° C. After 5 h, the reaction mixture was filtered through kieselguhr and the filter pad was washed with ethanol. The filtrate was then evaporated under reduced pressure to give the title compound as a yellow oil that crystallised on standing (6.68 g, 90%).

$^1$H NMR (200 MHz, $CDCl_3$) δ (ppm): 7.21 (dd, 1H), 7.12 (dd, 1H), 6.92 (d, 1H), 6.80 (d, 1H), 3.80 (s, 3H), 3.40 (t, 1H), 3.30 (m, 2H), 2.48 (m, 2H), 2.30 (s, 3H), 2.10 (m, 2H), 1.48 (m, 4H).

DESCRIPTION 3

3-(2-Methoxyphenyl)-8-tert-butoxycarbonyl-8-azabicyclo[3.2.1]octane 3-(2-Methoxyphenyl)-8-methyl-8-azabicyclo[3.2.1]octane (D2, 6.66 g, 0.029 mol) was dissolved in dichloromethane (200 ml) and was treated with 1-chloroethyl chloroformate (4.07 ml, 0.037 mol), followed by diisopropylethylamine (5.05 ml, 0.029 mol) with stirring at room temperature. After 20 h, the reaction mixture was evaporated under reduced pressure and the orange/brown oily residue was dried in vacuo. The oil was then redissolved in methanol (150 ml) and heated to reflux. After 0.5 h, the reaction mixture was allowed to cool and was evaporated under reduced pressure to give a brown oil. The oil was dried in vacuo and then redissolved in dichloromethane (100 ml). The resultant solution was then stirred at room temp. and triethylamine (4.50 ml, 0.032 mol) was added, followed by a solution of di-tert-butyl dicarbonate (6.96 g, 0.032 mol) in dichloromethane (50 ml). After 2 h, the reaction mixture was washed with water (2×), dried ($Na_2SO_4$) and evaporated under reduced pressure to give a brown oil, which was purified by silica-gel chromatography (1:1, petrol:diethyl ether) to give the title compound (8.84 g, 100%) as a colorless oil that crystallised on standing.

$^1$H NMR (200 MHz, $CDCl_3$) δ (ppm): 7.12 (d, 2H), 6.90 (d, 1H), 6.82 (d, 1H), 4.28 (m, 2H), 3.80 (s, 3H), 3.02 (m, 1H), 2.45 (m, 2H), 2.05 (m, 2H), 1.65 (m, 2H), 1.52 (s, 9H), 1.48 (m, 2H).

DESCRIPTION 4
3-(5-Amino-2-methoxyphenyl)-8-tert-butoxycarbonyl-8-azabicyclo[3.2.1]octane 3-(2-Methoxyphenyl)-8-tert-butoxycarbonyl-8-azabicyclo[3.2.1]octane (D3, 4.40 g, 0.014 mol) was dissolved in acetic anhydride (15 ml) and cooled to 0° C. Freshly ground copper (II) nitrate trihydrate (4.07 g, 0.017 mol) was then added with stirring over 15 minutes. The reaction mixture was then allowed to warm to room temperature. After 1 h, the reaction mixture was added slowly to an excess of sodium carbonate solution to give a pale blue suspension, which was extracted with dichloromethane (2×70 ml). The combined organic layers were then dried ($Na_2SO_4$) and evaporated under reduced pressure to give a brown oil which was partly purified by silica gel chromatography (2:1-1:1 petrol (60–80): $Et_2O$ as eluant) to give a pale yellow oil (1.34 g) which was redissolved in ethanol (50 ml) treated with 10% PdC (0.3 g) and hydrogenated at atmospheric pressure at 35° C. After 5 h, the reaction mixture was filtered through kieselguhr and the filter pad washed with ethanol.

The filtrate was then evaporated under reduced pressure and the resultant brown oil was purified by silica-gel chromatography (3:1, petrol (60–80): $Et_2O$) to give the title compound as a brown oil (0.550 g, 12%).

$^1$H NMR (200 MHz, $CDCl_3$) δ (ppm): 6.68 (d, 1H), 6.50 (m, 2H), 4.25 (m, 2H), 3.70 (s, 3H), 3.40 (s, 2H), 2.91 (m, 1H), 2.40 (m, 2H), 2.03 (m, 2H), 1.62 (m, 2H), 1.51 (s, 9H), 1.40 (m, 2H).

DESCRIPTION 5
3-(5-Amino-2-methoxyphenyl)-8-methyl-8-azabicyclo[3.2.1]octane 3-(5-Amino-2-methoxyphenyl)-8-tert-butoxycarbonyl-8-azabicyclo[3.2.1]octane (D4, 0.385 g, 1.16 mmol) was dissolved in dry THF (30 ml) with stirring and was treated with lithium aluminium hydride (0.088 g, 2.32 mmol) under argon. The reaction mixture was then heated to reflux. After 2 h and 4 h, further amounts of lithium aluminium hydride (0.132 g, 3.48 mmol) were added. Reflux was then maintained for a further 4 h, before the reaction mixture was allowed to cool. Water (0.352 ml) was then added, followed by 10% NaOH (0.528 ml) and water (0.880 ml). The mixture was then stirred for 0.5 h before being filtered through kieselguhr. The filter pad was then washed with THF (20 ml) and the filtrate evaporated under reduced pressure to give the title compound as a brown solid (0.242 g, 85%).

$^1$H NMR (250 MHz, $CDCl_3$) δ (ppm): 6.65 (d, 1H), 6.58 (d, 1H), 6.48 (dd, 1H), 3.70 (s, 3H), 3.40 (s, 2H), 3.30 (m, 1H), 3.20 (m, 2H), 2.38 (m, 2H), 2.22 (s, 3H), 2.08 (m, 2H), 1.50 (m, 2H), 1.40 (m, 2H)

DESCRIPTION 6
N-[3-(8-tert-Butoxycarbonyl-8-azabicyclo[3.2.1]octan-3-yl)-4-methoxyphenyl]-2'-methyl-4'-(5-methyl-1,2,4-oxadiazol-3-yl)biphenyl-4-carboxamide 3-(5-Amino-2-methoxyphenyl)-8-tert-butoxycarbonyl-8-azabicyclo[3.2.1]octane (D4, 0.130 g, 0.392 mmol) was transformed according to the method of Example 1 to give the title compound (0.202 g, 85%) as a cream foam.

$^1$H NMR (250 MHz, $CDCl_3$) δ (ppm): 8.02 (s, 1H), 7.95 (m, 3H), 7.81 (s, 1H), 7.48 (m, 4H), 7.32 (d, 1H), 6.82 (d, 1H), 4.28 (m, 2H), 3.80 (s, 3H), 3.05 (m, 1H), 2.70 (s, 3H), 2.45 (m, 2H), 2.31 (s, 3H), 2.05 (m, 2H), 1.65 (m, 2H), 1.51 (s, 9H), 1.45 (m, 2H)

DESCRIPTION 7
6-Methoxy-7-(8-methyl-8-azabicyclo[3.2.1]octan-3-yl) quinoline

The product from description 6 (0.642 g, 2.61 mmol) was treated with glycerol (0.360 g, 3.91 mmol), and iodine (0.014 g). Concentrated sulphuric acid (0.720 g, 7.57 mmol) was then added dropwise with stirring. The reaction mixture was then heated to 190° C. After 2 h, the reaction mixture was allowed to cool and the resultant brown gum was dissolved in water and 10% sodium hydroxide solution was added until pH14 was reached. The resultant suspension was then extracted with chloroform (4×). The combined extracts were then dried ($Na_2SO_4$) and evaporated under reduced pressure to give a dark brown oil which was dried in vacuo. The oil was purified by silica-gel chromatography (100:20:1 $CH_2Cl_2$:MeOH:$NH_3$ as eluant) to give the title compound as a pale brown oil (0.453 g, 62%)

$^1$H NMR (250 MHz, $CDCl_3$) δ (ppm): 8.71 (dd, 1H), 8.01 (d, 1H), 7.92 (s, 1H), 7.30 (dd, 1H), 7.0 (s, 1H), 3.90 (s, 3H), 3.55 (t, 1H), 3.30 (m, 2H), 2.53 (m, 2H), 2.30 (s, 3H), 2.12 (m, 2H), 1.58 (m, 4H).

DESCRIPTION 8
6-Methoxy-7-(8-methyl-8-azabicyclo[3.2.1]octan-3-yl]-1,2,3,4-tetrahydroquinoline The product from description 7 (0.443 g, 1.57 mmol) was dissolved in ethanol (50 ml) and was treated with $PtO_2$ (0.1 g). The resultant mixture was then hydrogenated at 50 psi. After 19 h, the reaction mixture was filtered through kieselguhr. The filter pad was washed with ethanol and the filtrate evaporated under reduced pressure and dried in vacuo to give the title compound as a cream foam (0.44 g, 98%).

$^1$H NMR (200 MHz, $CDCl_3$) δ (ppm): 6:50 (d, 2H), 3.72 (s, 3H), 3.60 (m, 2H), 3.48 (m, 1H), 3.22 (t, 2H), 2.70 (m, 4H), 2.60 (s, 3H), 2.20-1.85 (m, 9H).

DESCRIPTION 9
8-Methyl-3-trifluoromethylsulphonyloxy-8-azabicyclo[3.2.1]oct-2-ene A stirred solution of tropinone (1.70 g, 0.012 mol) in dry THF (20 ml) was cooled to −78° C. under argon and was treated with a solution of LDA (2.0M in heptane/THF/ethylbenzene) (6.50 ml, 0.013 mol). After 1 h, a solution of N-phenyltrifluoromethanesulphonimide (4.29 g, 0.012 mol) in dry THF (15 ml) was added at −70° C. After addition was complete, the cooling bath was removed and the reaction mixture was allowed to warm to room temp. After a further 16 h, the resulting pale yellow solution was evaporated under reduced pressure and dried in vacuo to give an orange oil. The oil was then purified by chromatography on neutral alumina (8.1 Petrol:EtOAc as eluant) to give the title compound as a yellow oil (2.34 g, 72%).

$^1$H NMR (250 MHz, CDCl$_3$) δ (ppm): 5.82 (d, 1H), 3.47 (m, 2H), 2.82 (dd, 1H), 2.40 (s, 3H), 2.20-1.90 (m, 4H), 1.65 (m, 1H).

DESCRIPTION 10
8-Methyl-3-(3-nitrophenyl)-8-azabicyclo[3.2.1]oct-2-ene

8-Methyl-3-trifluoromethylsulphonyloxy-8-azabicyclo[3.2.1]oct-2-ene (D9) (0.400 g, 1.48 mmol) was dissolved in DME (10 ml) and lithium chloride (0.188 g, 4.44 mmol) was added followed by 3-nitrobenzeneboronic acid (0.284 g, 1.70 mmol), and 2M sodium carbonate solution (4 ml). Argon was then bubbled through the mixture and after 5 minutes Pd(PPh$_3$)$_4$ (0.086 g, 0.074 mmol) was added. The mixture was then heated to reflux with stirring. After 4.5 h the reaction mixture was allowed to cool and was left at room temp. for 12 h, before being partitioned between chloroform and water. The aqueous layer was then extracted with chloroform (2×) and the combined organic layers were dried (Na$_2$SO$_4$) and evaporated under reduced pressure to give a brown oil that was dried in vacuo. The oil was purified by silica-gel chromatography (200:10.1, CH$_2$Cl$_2$MeOH:NH$_3$ as eluant) to give the title compound as a brown oil (0.147 g, 46%).

$^1$H NMR (200 MHz, CDCl$_3$) δ (ppm): 8.20 (t, 1H), 8.08 (dd, 1H), 7.70 (d, 1H), 7.50 (t, 1H), 6.42 (d, 1H), 3.52 (m, 2H), 2.95 (m, 2H), 2.49 (s, 3H), 2.30-2.00 (m, 2H), 1.95 (m, 1H), 1.62 (m, 1H).

DESCRIPTION 11
8-Methyl-3-(3-aminophenyl)-8-azabicyclo[3.2.1]octane

8-Methyl-3-(3-nitrophenyl)-8-azabicyclo[3.2.1]oct-2-ene (D10) (0.146 g, 0.598 mmol) was dissolved in ethanol (25 ml) and was hydrogenated at atmospheric pressure in the presence of 10% PdC (0.1 g) at 50° C. After 2 h, the reaction mixture was allowed to cool to room temp. and hydrogenation was continued for a further 16 h. The reaction mixture was then filtered through kieselguhr and the filter pad was washed with ethanol. The filtrate was then evaporated under reduced pressure to give the title compound as a pale yellow oil, which was dried in vacuo (0.104 g, 81%).

$^1$H NMR (250 MHz, CDCl$_3$) δ (ppm): 7.07 (t, 1H), 6.70 (d, 1H), 6.60 (s, 1H), 6.50 (dd, 1H), 3.65 (s, 2H), 3.33 (m, 2H), 3.00 (m, 1H), 2.50 (m, 2H), 2.38 (s, 3H), 2.05 (m, 2H), 1.75 (dd, 2H), 1.55 (d, 2H)

EXAMPLE 1
N-[3-(8-Azabicyclo[3.2.1 ]octan-3-yl)-4-methoxyphenyl]-2'-methyl-4'-(5-methyl-1,2,4-oxadiazol-3-yl)biphenyl-4-carboxamide The product from description 6 (0.194 g, 0.319 mmol) was dissolved in dichloromethane (4 ml) and was treated with trifluoroacetic acid (2 ml) dropwise with stirring. After 20 h, the reaction mixture was evaporated under reduced pressure and the residue partitioned between sodium hydrogen carbonate solution and dichloromethane. The aqueous layer was extracted with dichloromethane (1×) and the combined organic layers were dried (Na$_2$SO$_4$) and evaporated under reduced pressure to give the title compound as a yellow oil (0.160 g, 99%) which was subsequently converted to its oxalate salt.

m.pt. 230–232° C. (oxalate salt); $^1$H NMR (400 MHz, CD$_3$SOCD$_3$)(oxalate salt) δ (ppm): 10.20 (s, 1H), 8.08 (d, 2H), 7.98 (s, 1H), 7.91 (d, 1H), 7.82 (s, 1H), 7.65 (dd, 1H), 7.58 (d, 2H), 7.42 (d, 1H), 7.00 (d, 1H), 4.20 (br s, 2H), 4.04 (s, 2H), 3.80 (s, 3H), 3.35 (m, 1H), 2.70 (s, 3H), 2.42 (m, 2H) 2.35 (s, 3H), 1.95 (m, 4H), 1.85 (m, 2H).

EXAMPLE 2
N-[4-Methoxy-3-(8-methyl-8-azabicyclo[3.2.1]octan-3-yl) phenyl]-2'-methyl-4'-(5-methyl-1,2,4-oxadiazol-3-yl) biphenyl-4-carboxamide 2'-methyl-4'-(5-methyl-1,2,4-oxadiazol-3-yl)biphenyl-4-carboxylic acid (EPA 533268) was suspended in dichloromethane and treated with oxalyl chloride, followed by a drop of dry DMF, with stirring. After 2 h, the reaction mixture was evaporated under reduced pressure to give the crude acid chloride as a pale yellow solid which was dried in vacuo. The crude acid chloride was then redissolved in dichloromethane and triethylamine was then added, followed by a solution of the product from description 5 (0, 0.232 g, 0.943 mmol) in dichloromethane (2 ml) and the mixture was stirred at room temperature for 4 h before being washed with sodium bicarbonate solution (1×). The organic layer was then dried (Na$_2$SO$_4$) and evaporated under reduced pressure to give a brown oil which was purified by silica-gel chromatography to give the title compound (0.184 g, 38%) as a white foam. The title compound was subsequently converted to its oxalate salt.

mpt. 218–219° C. (oxalate salt); $^1$H NMR (400 MHz, CD$_3$SOCD$_3$) (oxalate salt) δ (ppm): 10.20 (s, 1H), 8.05 (d, 2H), 7.98 (s, 1H), 7.90 (m, 2H), 7.65 (dd, 1H), 7.55 (d, 2H), 7.41 (d, 1H), 7.00 (d, 1H), 4.45 (br s, 1H), 3.85 (s, 2H), 3.80 (s, 3H), 3.33 (m, 1H), 2.68 (s, 6H), 2.55 (m, 2H), 2.32 (s, 3H), 2.15 (m, 2H), 1.98 (m, 4H)

EXAMPLE 3
[3,4-Dihydro-6-methoxy-7-(8-methyl-8-azabicyclo[3.2.1] octan-3-yl)-2H-quinolin-1-yl]-[2'-methyl-4'-(5-methyl-1,2, 4-oxadiazol-3-yl)biphenyl-4-yl]methanone The product from description 8 (0.440 g, 1.54 mmol) was transformed to give the title compound (0.710 g, 82%) as a cream foam according to the methodology described in example 2 and was subsequently converted to its oxalate salt.

m.pt. 140–143° C. (oxalate salt); $^1$H NMR (400 MHz, CD$_3$SOCD$_3$ at 80° C.) (oxalate salt) δ (ppm): 7.92 (s, 1H), 7.88 (dd, 1H), 7.48 (d, 2H), 7.37 (d, 2H), 7.32 (d, 1H), 6.88 (s, 1H), 6.84 (s, 1H), 3.80 (m, 5H), 3.66 (m, 2H), 3.25 (m, 1H), 2.85 (t, 2H), 2.67 (s, 3H), 2.58 (s, 3H), 2.40–2.25 (m, 2H), 2.32 (s,3H), 2.10–1.98 (m, 4H), 1.60 (m, 2H), 1.48 (dd, 2H)

EXAMPLE 4
[7-(8-Azabicyclo[3.2.1]octan-3-yl)-3,4-dihydro-6-methoxy-2H-quinolin-1-yl]-[2'-methyl-4'-(5-methyl-1,2,4-oxadiazol-3-yl)biphenyl-4-yl]methanone The product from example 3 (0.350 g, 0.623 mmol) was dissolved in dichloromethane (15 ml) and was treated with 1-chloroethyl chloroformate (0.086 ml, 0.795 mmol), followed by diisopropylethylamine (0.138 ml, 0.795 mmol) with stirring under argon. After 20 h, the reaction mixture was evaporated under reduced pressure and the resulting brown foam was dissolved in methanol (20 ml), and heated to reflux with stirring. After 1 h, the reaction mixture was evaporated under reduced pressure and the brown oily residue was purified by silica-gel chromatography (100:10:1 CH$_2$Cl$_2$: MeOH: NH$_3$ as eluant) to give the title compound as a pale yellow oil (0.201 g, 59%), which was converted to its oxalate salt.

m.pt. 239–241° C. (oxalate salt); $^1$H NMR (250 MHz, CDCl$_3$)(free base) δ (ppm): 7.98 (s, 1H), 7.92 (d, 1H), 7.42 (d, 2H), 7.25 (m, 4H), 6.61 (s, 1H), 3.92 (t, 2H), 3.79 (s, 3H), 3.58 (m, 2H), 3.20 (m, 1), 2.83 (t, 2H), 2.68 (s, 3H), 2.32 (s, 3H), 2.10 (m, 6H), 1.80 (m, 2H), 1.42 (m, 2H), 0.95 (s, 1H).

EXAMPLE 5
N-[3-(8-Methyl-8-azabicyclo[3.2.1]octan-3-yl)phenyl]-2'-methyl-4'-(5-methyl-1,2,4-oxadiazol-3-yl)biphenyl-4-carboxamide 8-Methyl-3-(3-aminophenyl)-8-azabicyclo[3.2.1]octane (D11, 0.104 g, 0.481 mmol) was transformed to give the title compound as a cream solid (0.130 g, 55%) according to the method outlined in example 2, and was subsequently converted to its oxalate salt.

m.pt. 106–107° C. (oxalate salt); $^1$H NMR (250 MHz, CDCl$_3$)(free base) δ (ppm): 8.00 (m, 5H), 7.72 (s, 1H), 7.47 (m, 3H), 7.35 (m, 2H), 7.13 (d, 1H), 3.48 (s, 2H), 3.15 (m, 1H), 2.70 (s, 3H), 2.60 (m, 2H), 2.38 (s, 3H), 2.33 (s, 3H), 2.05 (m, 2H), 1.88 (dd, 2H), 1.60 (d, 2H).

We claim:

1. A compound of formula (I) or a salt thereof:

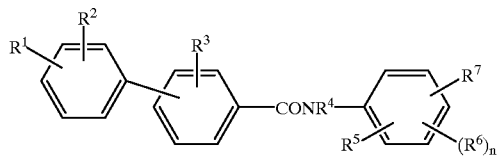

(I)

in which

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, CONHNR$^{10}$R$^{11}$, NR$^{10}$R$^{11}$, NR$^{10}$CO$_2$R$^{11}$, NR$^{10}$CO(CH$_2$)$_a$NR$^{10}$R$^{11}$, NR$^{10}$CONR$^{10}$R$^{11}$, CR$^{10}$=NOR$^{11}$, CNR$^{10}$=NOR$^{11}$, where R$^9$, R$^{10}$ and R$^{11}$ are independently hydrogen or C$_{1-6}$alkyl and a is 1 to 4 or R$^1$ is an unsubstituted or substituted 5 to 7-membered heterocyclic ring containing 1 to 3 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$_{11}$, NR$^{10}$R$^{11}$ where R$^{10}$ and R$^{11}$ are independently hydrogen or C$_{1-6}$alkyl;

R$^4$ is hydrogen or C$_{1-6}$alkyl and R$^5$ is hydrogen, halogen, hydroxy, C$_{1-6}$alkyl or C$_{1-6}$alkoxy or R$^4$ and R$^5$ together form a group —A— where A is (CR$^{12}$R$^{13}$)$_q$ where q is 2, 3 or 4 and R$^{12}$ and R$^{13}$ are independently hydrogen or C$_{1-6}$alkyl or A is (CR$^{12}$R 1)$_r$—D where r is 0, 1, 2 or 3 and D is oxygen, sulphur or CR$^{12}$=CR$^{13}$;

R$^6$ is hydrogen, halogen, hydroxy, C$_{1-6}$alkyl or C$_{1-6}$alkoxy;

n is 1 or 2; and

R$^7$ is an unsubstituted or substituted 6,6 or 6,5 bicyclic ring containing a nitrogen atom or R7 is an unsubstituted or substituted 6,6 or 6,5 bicyclic ring containing a nitrogen atom and a further heteroatom selected from from oxygen, nitrogen or sulphur.

2. A compound according to claim 1 in which R$^1$ is oxadiazolyl.

3. A compound according to claim 2 in which R$^2$ is C$_{1-6}$alkyl.

4. A compound according to claim 1 in which R$^3$ is hydrogen.

5. A compound according to claim 1 in which R$^4$ and R$^5$ are both hydrogen or R$^4$ with R$^5$ forms an ethyl or propyl group.

6. A compound according to claim 1 in which R$^6$ is C$_{1-6}$alkoxy.

7. A compound according to claim 1 in which R$^7$ is tropane or isoquinuclidine ring.

8. A compound according to claim 1 which is:

N-[3-(8-Azabicyclo[3.2.1]octan-3-yl)-4-methoxyphenyl]-2'-methyl-4'-(5-methyl-1,2,4-oxadiazol-3-yl)biphenyl-4-carboxamide, N-[4-Methoxy-3-(8-methyl-8-azabicyclo[3.2.1]octan-3-yl)phenyl]-2'-methyl-4'-(5-methyl-1,2,4-oxadiazol-3-yl)biphenyl-4-carboxamide,

[3,4-Dihydro-6-methoxy-7-(8-methyl-8-azabicyclo[3.2.1]octan-3-yl)-2H-quinolin-1-yl]-[2'-methyl-4'-(5-methyl-1,2,4-oxadiazol-3-yl)biphenyl-4-yl]methanone,

[7-(8-Azabicyclo[3.2.1]octan-3-yl)-3,4-dihydro-6-methoxy-2H-quinolin-1-yl]-[2'-methyl-4'-(5-methyl-1,2,4-oxadiazol-3-yl)biphenyl-4-yl]methanone, N-[3-(8-Methyl-8-azabicyclo[3.2.1]octan-3-yl)phenyl]-2'-methyl-4'-(5-methyl-1,2,4-oxadiazol-3-yl)biphenyl-4-carboxamide, or a pharmaceutically acceptable salt thereof.

9. A process for the preparation of a compound of formula (I) which comprises (a) for compounds where R$^4$ is hydrogen or C$_{1-6}$alkyl and R$^5$ is hydrogen, halogen, hydroxy, C$_{1-6}$alkyl or C$_{1-6}$alkoxy, reaction of a compound of formula (II):

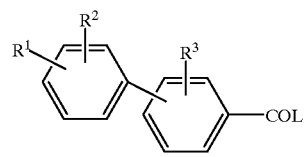

(II)

in which R$^1$, R$^2$ and R$^3$ are as defined in formula (I) and L is halogen or is an acid anhydride, ester or activated carboxylic acid forming group, with a compound of formula (III):

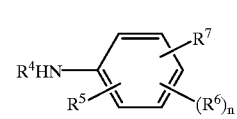

(III)

in which R$^4$ and R$^5$ are as defined above and R$^6$, R$^7$ and n are as defined in formula (I); or (b) for compounds where R$^4$ together with R$^5$ forms a group A, reaction of a compound of formula (II) as defined above with a compound of formula (IV):

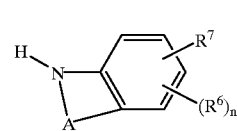

(IV)

in which A is as defined above and R$^6$, R$^7$ and n are as defined in formula (I); and optionally after (a) or (b) forming a pharmaceutically acceptable salt thereof.

10. A pharmaceutical composition which comprises a compound according to claim 1 in association with a pharmaceutically acceptable carrier or excipient.

11. A method of antagonizing the $5HT_{1D}$ receptor in a subject which comprises administering an effective amount of a compound of formula (I) as described in claim 1.

12. A method of treating depression, seasonal effective disorder, dysthymia, anxiety, panic disorder, agoraphobia, social phobia, obsessive compulsive disorder, post-traumatic stress disorder, dementia, age-associated memory impairment, anorexia nervosa, bulimia nervosa, Parkinson's disease, dementia in Parkinson's disease, neuroleptic-induced Parkinsonism, tardive dyskinesias which method involves treating a patient in need thereof with a therapeutically effective amount of a compound of claim 1.

13. A method of treating hyperprolactinaemia, vasospasm, hypertension and sexual dysfunction which method involves treating a patient in need thereof with a therapeutically effective amount of a compound of claim 1.

* * * * *